US012741846B2

(12) United States Patent
Saleh

(10) Patent No.: US 12,741,846 B2
(45) Date of Patent: Sep. 22, 2026

(54) SMART ACCESS CONTROL SYSTEM AND DEVICE FOR ELEVATORS

(71) Applicant: Ahmad Saleh, Dubai (AE)

(72) Inventor: Ahmad Saleh, Dubai (AE)

(73) Assignee: Ahmad Saleh, Dubai (AE)

(*) Notice: Subject to any disclaimer, the term of this patent is extended or adjusted under 35 U.S.C. 154(b) by 1325 days.

(21) Appl. No.: 17/543,084

(22) Filed: Dec. 6, 2021

(65) Prior Publication Data

US 2022/0242693 A1 Aug. 4, 2022

Related U.S. Application Data

(60) Provisional application No. 63/144,502, filed on Feb. 2, 2021.

(51) Int. Cl.

| | |
|---|---|
| ***B66B 1/46*** | (2006.01) |
| ***A61B 5/01*** | (2006.01) |
| ***B66B 1/34*** | (2006.01) |
| ***G06F 21/32*** | (2013.01) |
| ***H04W 88/02*** | (2009.01) |

(52) U.S. Cl.

CPC ................ *B66B 1/468* (2013.01); *A61B 5/01* (2013.01); *B66B 1/3446* (2013.01); *G06F 21/32* (2013.01); *B66B 2201/103* (2013.01); *B66B 2201/4615* (2013.01); *B66B 2201/4623* (2013.01); *B66B 2201/4638* (2013.01); *B66B 2201/4653* (2013.01); *H04W 88/02* (2013.01)

(58) Field of Classification Search

CPC . B66B 1/468; B66B 1/3446; B66B 2201/103; B66B 2201/4615; B66B 2201/4623; B66B 2201/4638; B66B 2201/4653; B66B 2201/4676; A61B 5/01; G06F 21/32; G06F 21/35; H04W 88/02

See application file for complete search history.

(56) References Cited

U.S. PATENT DOCUMENTS

| | | | | |
|---|---|---|---|---|
| 6,615,175 B1 * | 9/2003 | Gazdzinski | ............. | B66B 3/006 704/E15.045 |
| 7,093,693 B1 * | 8/2006 | Gazdzinski | ............... | B66B 3/00 340/5.2 |

(Continued)

FOREIGN PATENT DOCUMENTS

| | | | | |
|---|---|---|---|---|
| CN | 106115391 A * | 11/2016 | ........... | B66B 1/3415 |
| CN | 107000969 A * | 8/2017 | ............... | G07C 9/27 |

(Continued)

*Primary Examiner* — Jeffrey Donels

(57) ABSTRACT

There is provided a smart access control device (SACD) for access control to an elevator system, the SACD comprising a receiver, a processing unit, and a communication unit for receiving by the receiver an identifier from a user device associated to a user and for automatically determining by the processing unit a destination floor associated to the user based on the identifier received and access control data stored in a storage unit accessible to the processing unit, and for generating and transmitting a signal to the elevator system for automatically initiating an elevator car trip for the user to the destination floor determined by the processing unit. There is also provided a user device configured to be in communication with a smart access control device (SACD) for access control to an elevator system.

16 Claims, 13 Drawing Sheets

(56) References Cited

U.S. PATENT DOCUMENTS

| | | | | |
|---|---|---|---|---|
| 7,711,565 | B1 * | 5/2010 | Gazdzinski | B66B 1/468 369/30.01 |
| 11,113,913 | B1 * | 9/2021 | Doherty | H04L 67/12 |
| 12,183,469 | B1 * | 12/2024 | Warnick | G16H 15/00 |
| 2018/0162688 | A1 * | 6/2018 | Troesch | B66B 1/468 |
| 2018/0247043 | A1 * | 8/2018 | Chang | G07C 9/00 |
| 2018/0247070 | A1 * | 8/2018 | Evans | G08B 25/12 |
| 2019/0084794 | A1 * | 3/2019 | Scoville | B66B 1/468 |
| 2019/0100405 | A1 * | 4/2019 | Scoville | B66B 1/3415 |
| 2020/0130983 | A1 * | 4/2020 | Karve | B66B 1/2458 |
| 2022/0185622 | A1 * | 6/2022 | Miriyala | B66B 5/0012 |

FOREIGN PATENT DOCUMENTS

| | | | | |
|---|---|---|---|---|
| EP | 3290374 | A1 * | 3/2018 | B66B 1/468 |
| KR | 200359849 | Y1 * | 8/2004 | B66B 1/468 |
| WO | WO-2016165782 | A1 * | 10/2016 | B66B 1/468 |
| WO | WO-2017175023 | A1 * | 10/2017 | B66B 3/006 |

* cited by examiner

SMART ACCESS CONTROL SYSTEM AND DEVICE FOR ELEVATORS

CROSS-REFERENCE TO RELATED APPLICATIONS

The present invention claims priority from the previously filed U.S. Provisional Patent Application No. 63/144,502 filed Feb. 2, 2021. This patent application is herein incorporated in its entirety.

FIELD OF THE INVENTION

The present invention relates to access control systems and devices for elevators, and more particularly to a smart access control system, device and process for access control to an elevator system for automatic and seamless access to elevator services.

BACKGROUND OF THE INVENTION

Background description includes information that may be useful in understanding the present invention. It is not an admission that any of the information provided herein is prior art or relevant to the presently claimed invention, or that any publication specifically or implicitly referenced is prior art.

In today's busy and running life, the world is moving towards automation and so is the technology. Even the technology today is advancing by bringing in provisions to speed up the tasks and also to make them easy. Further, the COVID-19 and other infectious diseases have changed the way people and businesses operate. Social distancing is nowadays a must in order to prevent the spread of such infectious diseases. Unfortunately, with the release of lock-downs, businesses and governments are still struggling to find solutions for securing the health and safety of their people. As a precautionary measure, the concerned authorities have made it compulsory for the users to wear face masks, face shields, gloves, etc. at public places like offices, shopping malls, etc. This practice is not even sufficient to prevent the spread of the virus. Whenever one steps out, he/she is required to touch several things that may increase the risk of spread of virus.

As a precautionary measure, there is only a provision of checking the proper use of gloves, etc, by the user by human security guards at the gate entries which is ineffective in many cases. Conventionally, the security guard checks the proper use of gloves by the user by a cursory glance and accordingly allows the person to enter the premises. However, if the user is found to be not properly using gloves, the security guard does not provide the access to the user till he/she properly puts on the safety equipments. The above practice is susceptible to failure. Firstly, it is somewhat difficult for the human security guard to keep a check round the clock and so might there might be few occasions like overcrowding, odd hours, etc. when the guard may fail to properly check the visitors. Also, for the process to be effective, the guard is required to check the visitors so carefully as even if one infected person is allowed enter the premises, he may spread the infection to several others. Even if the guard is not present at the gate for a moment, several people can enter without even getting tested. Further, the process is time taking which is not even favourable to the users and it also includes human interaction which is again likely to trigger the spread of the infection.

Also, there are certain zones which require a more attention for safety, security and infection control for the security, safety and/or infection risk associated to these places of example (such as highly crowded areas or narrow spaces with small distances between persons). There is a need to restrict access to curtained controlled zones to people wearing/using complying with certain safety, health and security requirements. Traditional access controls systems fail to provide such a control in an automated and technologically smart manner.

Therefore, there is a need to automatically control access to the certain controlled zones minimizing the human intervention. Traditional access controls systems fail to provide such a control in an automated and technologically smart manner.

SUMMARY OF THE INVENTION

As a first aspect of the invention, there is provided a smart access control device (SACD) for access control to an elevator system, the SACD comprising a receiver, a processing unit, and a communication unit for receiving by the receiver an identifier from a user device associated to a user and for automatically determining by the processing unit a destination floor associated to the user based on the identifier received and access control data stored in a storage unit accessible to the processing unit, and for generating and transmitting a signal to the elevator system for automatically initiating an elevator car trip for the user to the destination floor determined by the processing unit.

As another aspect of the invention, there is provided a user device configured to be in communication with a smart access control device (SACD) for access control to an elevator system, the SACD automatically determining a destination floor and triggering an elevator car trip associated to the user to the destination floor based on an identifier received from the user device using said communication and access control data stored in a storage unit accessible to the SACD.

As a further aspect of the invention, there is provided a smart access control system for access control to a plurality of elevator systems, the system comprising (a) plurality of smart access control devices, each one comprising a receiver, a processing unit, and a communication unit for receiving by the receiver identifiers from user devices associated to users and for automatically determining by the processing unit destination floors associated to the users based on the identifiers received and access control data stored in a storage unit accessible to the processing unit, and for generating and transmitting signals to the elevator systems for automatically initiating elevator car trips for the users to the destination floors; (b) a server in communication with the plurality of smart access control devices for centrally and dynamically setting and managing access control rules associated to the users and elevator systems, and communicating these to the plurality of smart access control devices.

Preferably, the access control data comprises identifiers related to user devices mapped to corresponding destination floors.

Preferably, the identifiers are unique identifiers such as each identifier allows to uniquely identify at least one of the user of the destination floor.

The storage unit can be a cloud-based storage unit, and in this case the SACD further comprises a communication unit in remote communication with the cloud-based storage unit.

Preferably, the user device is automatically detected and the identifier is automatically transmitted from the user device to the SACD when the user device is within a specific elevator zone, and the determination of the destination floor and the signal generation and transmission to the elevator system for automatically initiating an elevator car trip are automatically conducted seamlessly without any user or other human interaction.

Preferably, the receiver comprises an Ultra High Frequency RFID reader configured to detect the user device only when the user device is within the specific elevator zone.

Preferably, the specific elevator zone is inside the elevator.

Preferably, the automatically initiating an elevator car trip for the user to the destination floor is conducted seamlessly without any user or other human interaction.

Preferably, the communication between the user device and the SACD is a wireless communication.

Preferably, the identifier is a unique identifier allowing to uniquely identify at least one of the user and the destination floor.

Preferably, the user device is a remote control comprising a user interface for triggering the communication with the SACD and a transmitter for transmitting the identifier through the communication.

Preferably, the user device further comprises a biometric unit for authenticating the user prior to and as a condition to communicating with the SACD.

The user device may also be completely seamless; the user device may comprise an RFID transceiver and the identifier is an RFID identifier.

The user device may also comprise a biometric system for identifying the user based on biometric data obtained from the user.

The user device preferably further comprises a health & safety monitoring unit configured to detect a health or safety condition associated to the user, wherein the SACD controls access of the user to the elevator system based on the detected health or safety condition of the user. Preferably, the health & safety monitoring unit comprises a temperature sensor for detecting a temperature of the user, and wherein access to the elevator system is only granted if the user's temperature detected is below a given threshold.

The user device may be a wearable device selected from the group consisting of a ring and a bracelet.

Preferably, the server in communication with the smart access control system is a cloud-based server configured to divide the users based on their identifiers in a plurality of categories, wherein each category has its respective access control rules.

BRIEF DESCRIPTION OF DRAWINGS

The subject matter that is regarded as the invention is particularly pointed out and distinctly claimed in the claims at the conclusion of the specification. The foregoing and other aspects, features, and advantages of the invention are apparent from the following detailed description taken in conjunction with the accompanying drawings in which:

DETAILED DESCRIPTION OF THE INVENTION

Figure 1:
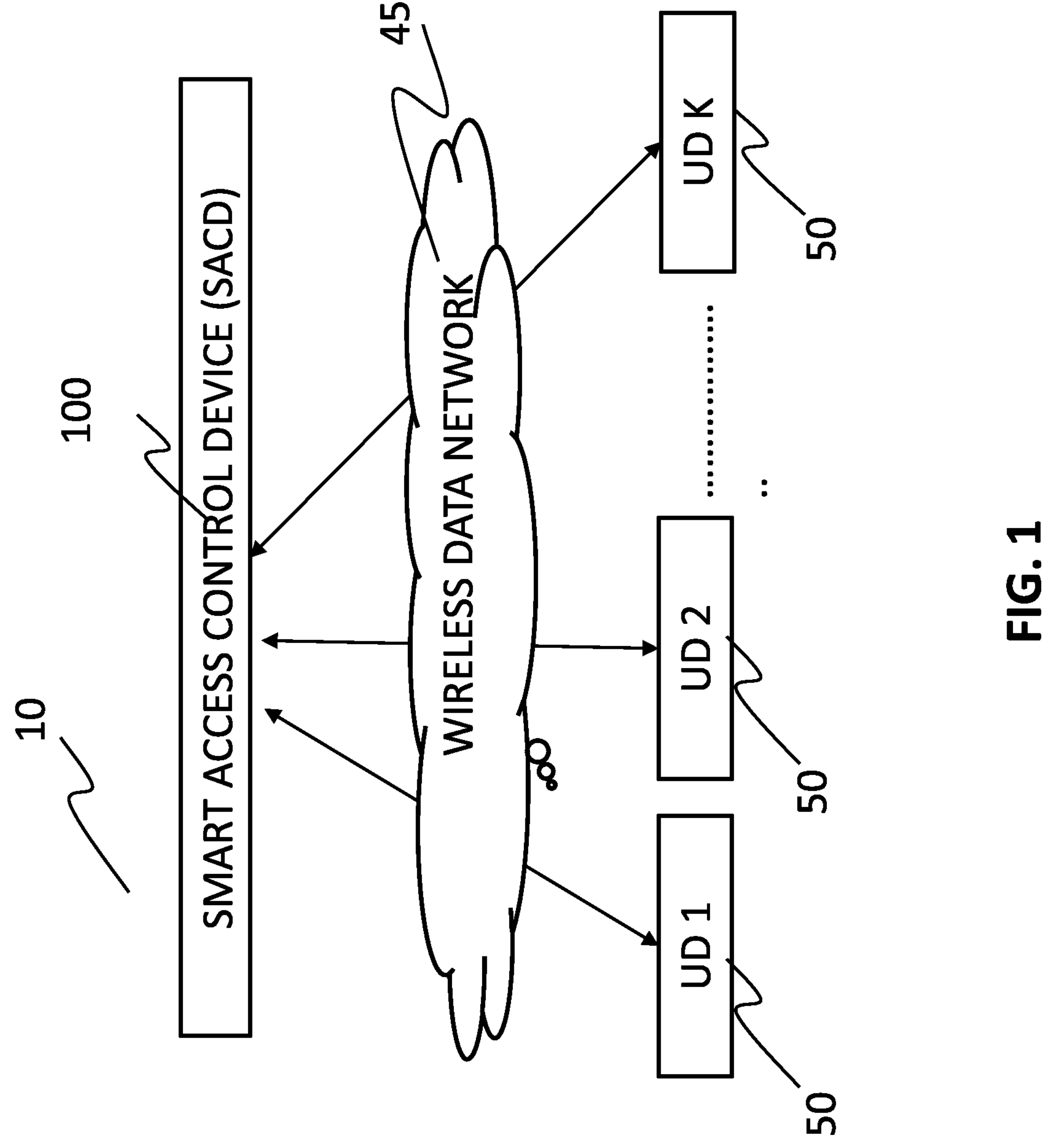
FIG. 1 is a block diagram illustrating a smart access control system (SACS) comprising a smart access control device (SACD) and a plurality of user devices for elevators in accordance with an embodiment of the invention.

For the purpose of promoting an understanding of the principles of the invention, reference will now be made to the embodiment illustrated in the drawings, and specific language will be used to describe the same. It will nevertheless be understood that no limitation of the scope of the invention is thereby intended. Such alterations and further modifications in the illustrated system, and such further applications of the principles of the invention as illustrated therein would be contemplated as would normally occur to one skilled in the art to which the invention relates. Unless otherwise defined, all technical and scientific terms used herein have the same meaning as commonly understood by one of ordinary skilled in the art. The system, methods, and examples provided herein are illustrative only and are not intended to be limiting.

The term "some" as used herein is to be understood as "none or one or more than one or all." Accordingly, the terms "none," "one," "more than one," "more than one, but not all" or "all" would all fall under the definition of "some." The term "some embodiments" may refer to no embodiments or to one embodiment or to several embodiments or to all embodiments, without departing from the scope of the present disclosure. The terminology and structure employed herein is for describing, teaching, and illuminating some embodiments and their specific features. It does not in any way limit, restrict or reduce the spirit and scope of the claims or their equivalents.

More specifically, any terms used herein such as but not limited to "includes," "comprises," "has," "consists," and grammatical variants thereof do not specify an exact limitation or restriction and certainly do not exclude the possible addition of one or more features or elements, unless otherwise stated, and furthermore must not be taken to exclude the possible removal of one or more of the listed features and elements, unless otherwise stated with the limiting language "must comprise" or "needs to include." Whether or not a certain feature or element was limited to being used only once, either way, it may still be referred to as "one or more features" or "one or more elements" or "at least one feature" or "at least one element." Furthermore, the use of the terms "one or more" or "at least one" feature or element do not preclude there being none of that feature or element, unless otherwise specified by limiting language such as "there needs to be one or more . . . " or "one or more element is required."

Unless otherwise defined, all terms, and especially any technical and/or scientific terms, used herein may be taken to have the same meaning as commonly understood by one having ordinary skills in the art. Reference is made herein to some "embodiments." It should be understood that an embodiment is an example of a possible implementation of any features and/or elements presented in the attached claims. Some embodiments have been described for the purpose of illuminating one or more of the potential ways in which the specific features and/or elements of the attached claims fulfill the requirements of uniqueness, utility and non-obviousness.

Use of the phrases and/or terms including, but not limited to, "a first embodiment," "a further embodiment," "an alternate embodiment," "one embodiment," "an embodiment," "multiple embodiments," "some embodiments," "other embodiments," "further embodiment", "furthermore embodiment", "additional embodiment" or variants thereof do not necessarily refer to the same embodiments. Unless otherwise specified, one or more particular features and/or elements described in connection with one or more embodiments may be found in one embodiment, or may be found in more than one embodiment, or may be found in all embodiments, or may be found in no embodiments. Although one or more features and/or elements may be described herein in the context of only a single embodiment, or alternatively in the context of more than one embodiment, or further alternatively in the context of all embodiments, the features and/or elements may instead be provided separately or in any appropriate combination or not at all. Conversely, any features and/or elements described in the context of separate embodiments may alternatively be realized as existing together in the context of a single embodiment.

Any particular and all details set forth herein are used in the context of some embodiments and therefore should not be necessarily taken as limiting factors to the attached claims. The attached claims and their legal equivalents can be realized in the context of embodiments other than the ones used as illustrative examples in the description below. Embodiments of the present invention will be described below in detail with reference to the accompanying drawings.

Referring to FIG. 1, there is provided a Smart Access Control System (SACS) 10 for controlling access of users to an elevator 15 based on a status of the user. The status of the user, may comprise access rights of the user to restricted floors of a building. Users may be identified through one or more user devices 50. The user devices 50 may be a handheld device or a portable device. The user devices 50 may be allocated to users on a 1:1 exclusivity basis such that each user device 50 is allocated to one given user, and such that an identification of the user device 50 leads to an identification of the user. The user devices 50 may also be allocated on a non-exclusivity basis such that a user device 50 may be used by more than one users for use/identification purposes. An example of a non-exclusivity user device 50 is a face or biometric recognition system.

Figure 2:
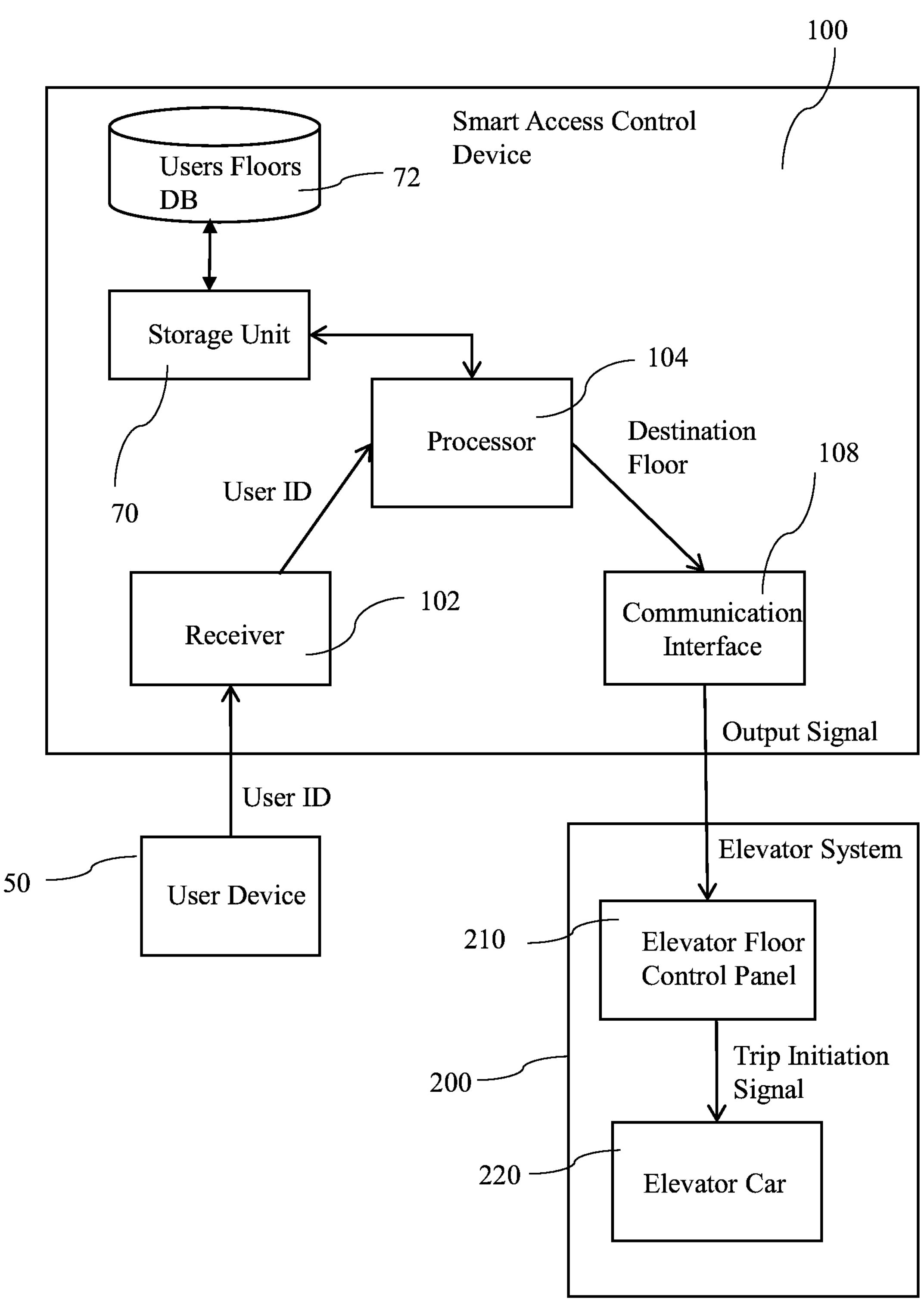
FIG. 2 is a block diagram illustrating a smart access control device (SACD) in communication with an elevator system and a user device in accordance with an embodiment of the invention.

The status of the user may also comprise a legal or regulatory status or profile of the user such as legal status inside a country, work permit status, country of citizenship or residency, regulatory compliance and so on. The status of the user may also comprise compliance requirements, such as health and safety conditions associated to the users such as real time health conditions of the users or pre-stored health data such as medical check out history and previously generated medical tests in order to enhance compliance, safety, security and control spread of infectious diseases between the users and others inside the elevator 15. Referring to FIG. 2 there is provided a SACD 100 for controlling access of a user to an elevator 15, comprising automatically determining a destination elevator floor accessible to a user (elevator passenger) and initiating an elevator car trip for the user to the determined destination floor. In an embodiment of the invention, the SACD 100 comprises a receiver 102 for obtaining an identifier from a user device 50. The SACD 100 further comprises a processor 104 in communication with a storage unit 70 for determining a destination floor associated to the user based on the identifier received from the user device 50 and access control data pre-stored in the storage unit 70. The access control data may comprise user related data, such as floor numbers allowed/accessible to the user.

An identifier may be referred to in this application as a signal in any form or shape such as an electrical signal, an optical signal, an electromagnetic signal, an ultrasound signal, a number, code, alphanumerical code, or any other type of identification. In an embodiment of the invention, as illustrated in FIG. 1, the SACD 100 comprises the storage unit 70 which is locally connected to the processor 104.

The user-related data pre-stored in the storage unit 70 may comprise a Users Floors DB comprising identifiers mapped to corresponding destination floors. Each identifier among the identifiers may be mapped to a given destination floor among the elevator floors associated to a given user. The pre-stored identifiers may be associated to respective registered users, such that each pre-stored identifier may be associated to a corresponding user. The pre-stored destination floors may refer to restricted floors accessible to the registered users only, such that each identifier may be indicative of a floor accessible to a specific user.

The SACD 100 further comprises a communication unit 108 in communication with the processor 104. The processor 104, once a destination floor associated to a given received identifier is determined, generates and transmits a signal to the communication unit 108 with an indication of the destination floor associated to the identifier received. The communication unit 108 in adapted/configured to be in communication with the elevator system 200 for generating and transmitting an output signal to the elevator system 200 for automatically initiating an elevator trip of the user to the destination floor. The output signal may be generated in accordance with a suitable communication protocol adapted to be readable by the elevator system 200, depending on the type of the elevator system 200. In an embodiment of the invention, the SACD 100 may comprise an elevator capacity counter unit or module (not shown) which is configured to control the number of users within the same elevator car, and to reject requests received from users to access the elevator services based on the capacity of the elevator, which may be measured in terms of maximum number of users allowed to be in the same elevator car at any given time. The number of persons inside an elevator may be determined by the SACD 100 based on the number of new users requesting the elevator services (through new identifiers received) and the number of users already serviced (though identifiers previously received). The total number of users within an elevator car at any given time may be measured by the total number of identifiers received while the elevator is stationary at any given floor, minus the total number of identifiers received previously relative to the given floor where the elevator is stationary (as the users being routed to the current floor would have exited the elevator car). The elevator capacity control unit (not shown) may comprise an imaging system (not shown) configured to determine the number of users at any given time, and to reject elevator access services to any new users when the elevator capacity is met. The elevator may also have a person counter/detector for counting the number of persons entering and exiting the elevator and determining the number of users inside an elevator car at any given time.

Figure 3:
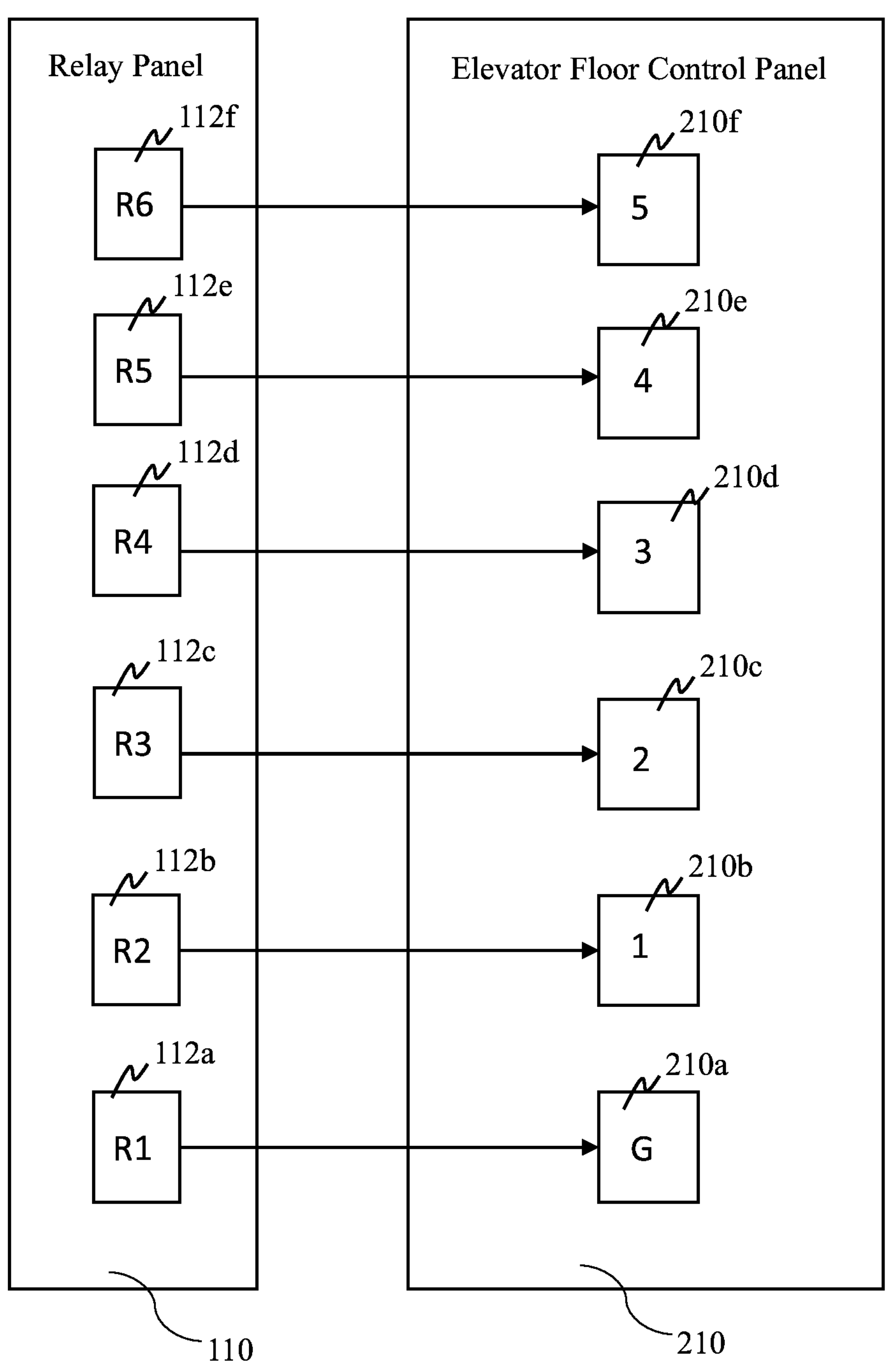
FIG. 3 is a block diagram illustrating a connection between a SACD Relay Panel and an elevator floor control panel in accordance with an embodiment of the invention.

In an embodiment of the invention, as illustrated in FIG. 3, the communication interface 108 may comprise a relay panel 110 comprising one or more relays (112*a*, 112*b* . . . 112*f*) respectively corresponding to one or more elevator floors. Each relay in the relay panel 110 may correspond to a respective elevator floor among the elevator floors. The processor 104 may send an activation signal to the relay corresponding to the destination floor as determined by the processing unit 104. The processor 104 may be configured with a table mapping each floor of the elevator floors to a corresponding relay in the relay panel 110. The destination floor signal generated by the processor 104 may be transmitted to the given relay among the relays (112*a* to 112*f*) of the relay panel 110 which corresponds to the destination floor determined by the processor 104. The relay panel 108 may be connected to the elevator system 200 for transmitting thereto an output signal for initiating an elevator trip to the destination floor associated to the user.

In an embodiment of the invention, the relay panel 110 may be connected to the elevator control panel/buttons keyboard 210. The relays (112*a* to 112*f*) in the relay panel 110 may be connected to their respective floor connections/buttons (212*a*, 212*b*, . . . , 212*f*) in the elevator control panel/buttons keyboard 210. For example, when a given destination floor "X" is determined by the processor 104, the processor 104 activates the relay "X" in the relay panel 110 corresponding to the floor "X". The relay "X" outputs a signal to the connection/button in the elevator panel/keyboard 200 corresponding to the floor "X". The elevator panel/keyboard 200 is connected to the elevator car 220 (and corresponding lift system) for automatically initiating a trip of the elevator car to the destination floor "X". Following the receipt of the identifier by the receiver 102, the entire process is conducted automatically and seamlessly without any human interaction or intervention. The user is not required to touch a device or a system, such as the keyboard of the elevator, to initiate the elevator car trip.

Figure 4:
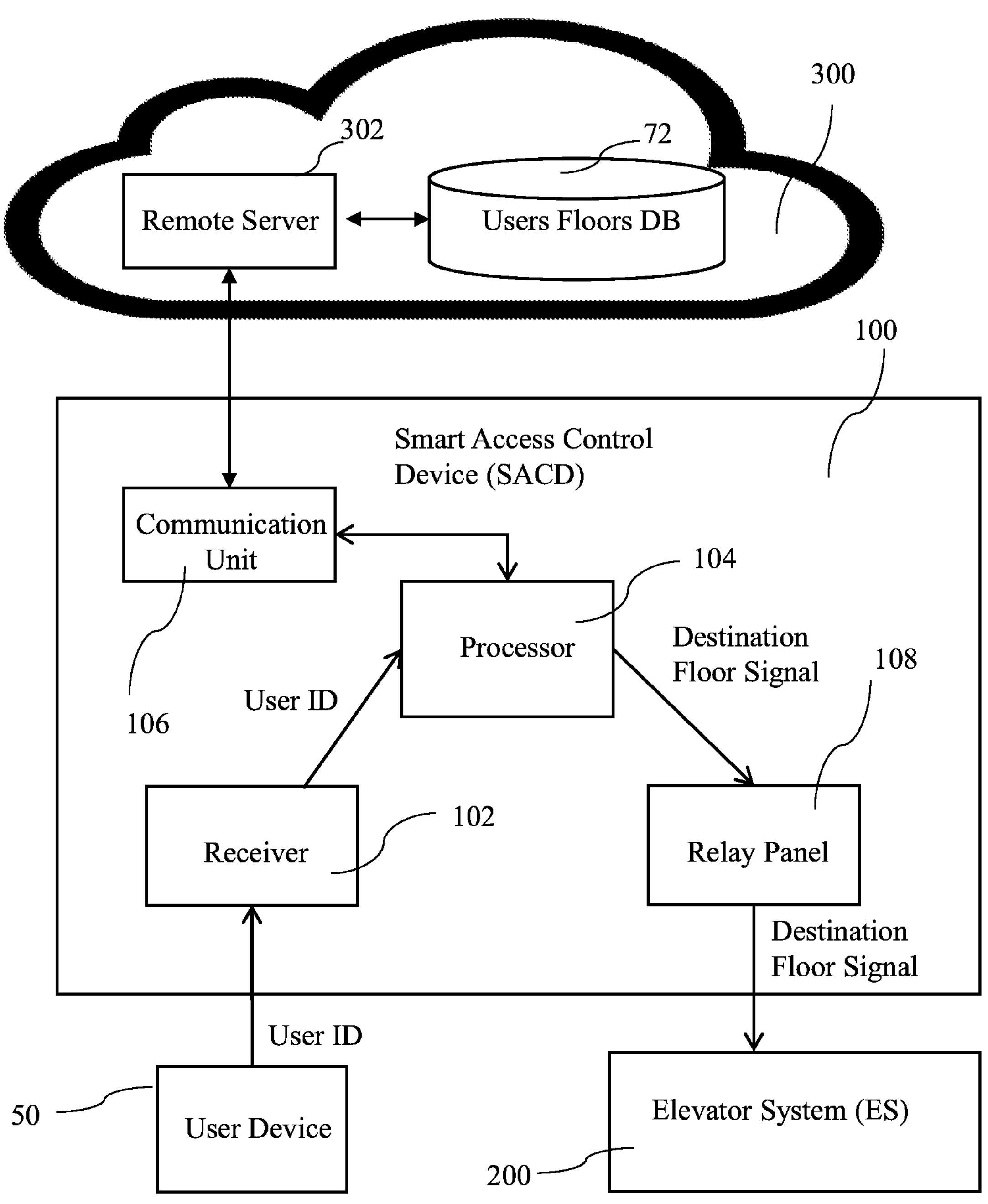
FIG. 4 is a block diagram illustrating a SACD in communication with a cloud-based remote server in accordance with an embodiment of the invention.
Figure 5:
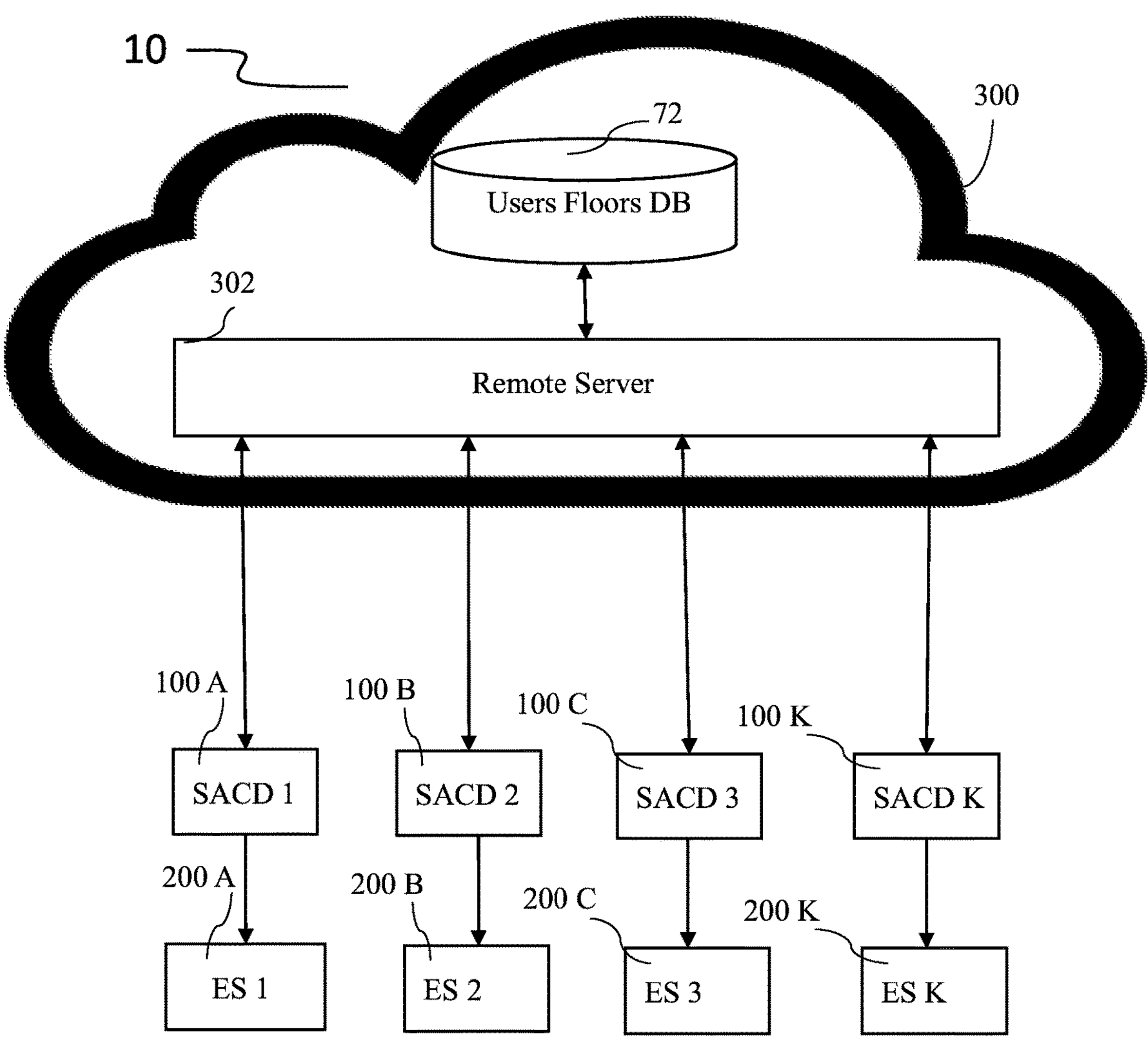
FIG. 5 is a block diagram illustrating a SACS comprising a plurality of SACDs in communication with a cloud-based remote server in accordance with an embodiment of the invention.

In an embodiment of the invention, as illustrated in FIG. 4, the users floors database 72 may be located on a data cloud 300 remotely connected to the SACD 100. According to this embodiment, the SACD 100 may comprise a communication unit 106 in remote communication with a cloud-based remote server 302 connected to the users floors database 72. The processor 104 queries the remote server 302 using the received identifier for retrieving the corresponding destination floor as stored in the users floors database 72. The remote server 302 may also configured to update the users floors database 72 based on input data from the communication unit 106, or another interface. The communication unit 106 may comprise a GSM module for establishing a data link between the processor 104 and the remote server 302. In an embodiment of the invention, as illustrated in FIG. 5, the remote server 302 may be connected to a plurality of SACDs (100A, . . . , 100K) respectively connected to a plurality of elevator systems (200A, . . . , 200K) for automatically determining destination elevator floors accessible to users (elevator passengers) based on identifiers received from user devices 50 and automatically and without human interaction initiating elevator car trips for the users to the determined destination floors.

The user device 50 may provide a seamless floor selection and elevator car trip to using the wireless communication with the receiver 102. The seamless user device 50 may provide automated floor selection and elevator car trip initiation to a plurality of elevators within different buildings. E. The user may have different access rights within each building. For example, in Building A, the user may have access to floor 5 only, whereas the user may have access rights to floor 10 only in Building B. The user, through its associated identifier associated to his/her user device 50 may be automatically routed to his corresponding floors within both buildings A and B. A single user device 50 may enable the user to have seamless/automated access and elevator car trips to his respective floors in various buildings. In an embodiment, a user may carry a single user device 50. An RFID system may be installed at a plurality of elevators. For example, a first SACD 100 of elevator A may receive the user identifier, and routes the user to floor 13 of the building based on the pre-stored information, where a second SACD 100 of elevator B in another building may receive the same user identifier, and routes the user to floor 2 (of said other building) based on pre-stored information. This is as the same user may have different access rights in different buildings.

Figure 6:
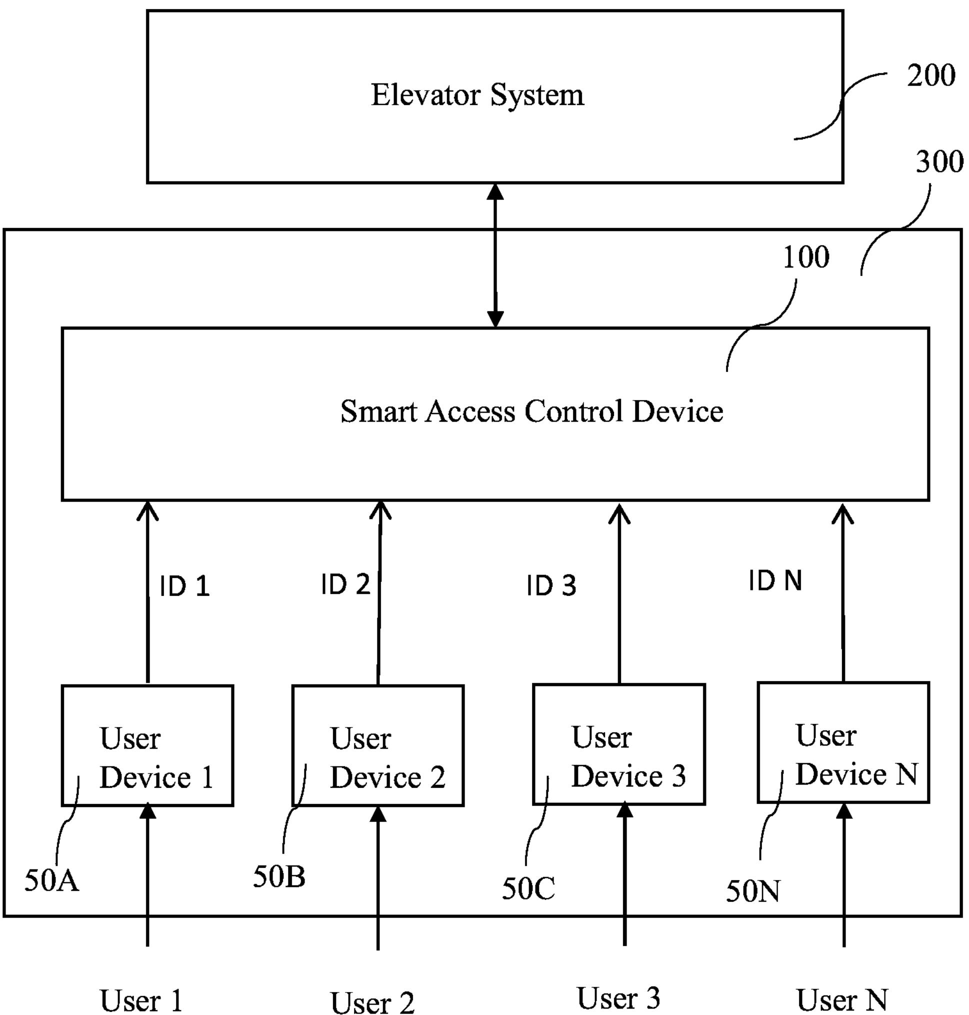
FIG. 6 is a block diagram illustrating a SACD in communication with user devices for obtaining their respective IDs in accordance with an embodiment of the invention.

In an embodiment of the invention, as illustrated in FIG. 6, there is provided a Smart Access Control System (SACS) 10 for elevators comprising a SACD 100 and a plurality of user devices 50 having respective identifiers in accordance with the various embodiments of the invention. The plurality of user devices 50 are allocated to respective users such that each user is provided with a user device 50 configured with one or more identifiers readable by the SACD 100. The system 300 is configured such that once an identifier associated to a user is received from a user device 50, the system 10 automatically maps the identifier received to a destination floor associated to the user and automatically initiates an elevator car trip to the destination floor, and this without any human interaction or intervention.

In an embodiment of the invention, each user device 50 among the plurality of user devices 50 is provided with a unique identifier which is configured to uniquely identify the user and/or the user device and/or the destination floor. The identifiers are stored in the storage unit 70 and are mapped to respective destination floors in accordance with the various embodiments of the present invention. The user devices 50 with the respective identifiers may be mapped to the various elevator floors such that each elevator floor (or each restricted floor) is mapped to one or more identifiers associated with respective user devices 50. In an embodiment of the invention, the user devices 50 may then be allocated to the users based on their restrictive floors to where they are allowed access. For example, users working at Floor 5 are allocated with "Floor 5" user devices having "Floor 5" pre-configured identifiers mapped to destination Floor 5, such that when these "Floor 5" pre-configured identifies are received by the SACD 100, the users are automatically routed to destination floor 5 by automatically initiating elevator car trips to these destination floors.

For example, a facility management of a building of N floors having X registered employees and potential visitors in each floor may for example organize user devices 50 into categories (Category Floor 1, Category Floor 2, . . . , Category Floor N) and dedicate X user devices for each floor of the building such that Group 1 User Devices comprise X user devices with associated identifiers mapped to destination floor 1, Group 2 User Devices comprise X user devices with associated identifiers mapped to destination floor 2, . . . , Group N User Devices comprise X user devices with associated identifiers mapped to destination floor N. In an embodiment of the invention, each user device 50 has a unique identifier configured to uniquely identify the device/the associated user. In this case, the identifiers associated to the various user devices 50 may be mapped to respective users such that each user would have a unique user device identifier. Data mapping these identifies to the destination floors associated to the respective users may be stored inside the storage unit 70. When an identifier is received, the processor 104 queries the storage unit 70 using the identifier received for determining the associated destination floor. The SACD 100 uses this information to communication with the elevator system 200 for initiating an elevator car trip to the destination floor associated to the identifier.

In an embodiment of the invention, access details associated to the users using the elevators may be stored and kept in records for further use. The access details may be stored in the storage unit 70 or in a separate database. Alternatively, this information may be sent remotely through a data network such as a telephone network or TCP/IP. The access details may comprise as list of the identifiers which have accessed an elevator during a given period of time, along with the corresponding access date/time and destination floor. These access details may be used by the facility management for management purposes (such as employee attendance, contact tracking/traceability, and other purposes). In an embodiment of the invention, a separate management database/software may be provided/used to map the identifiers to user personal information such as employee/staff number and so on. As the SACD 100 may be provided and managed by a private entity different from the facility management entity/authority, this method may preserve data privacy associated to the users such that the private entity managing the access control does not hold personal information associated to the users. The private entity managing access control may only hold data representing user/device identifiers mapped to destination floors. These identifiers may only be used to identify the persons of the users (their real identity) when these identifiers are mapped to the users' personal information, which may be done only by the facility management entity/authority through a separate database/system which may already hold personal information associated to the users and accredited to hold personal confidential information.

In an embodiment of the invention, the facility management entity/authority requires the access control management entity to provide X number of user devices 50 for each floor among the N floors of the facility. For each floor, X user devices are provided with X unique identifiers respectively associated to the user devices 50. The private access control management company stores the access control data in the storage unit 70 mapping the X unique identifiers to the associated floors (destination floors). In an embodiment, the users identified by the SACD 100 at any given time may be compiled, preferably dynamically and in real time, and highlighted on a map based on one or more pre-stored information mapping the identifier to a specific floor using their respective collected user related data and/or user identifier. A mobile application configured with a map may be provided in communication with the SACS 10. A management system may also be provided in communication with the SACS 10 for dynamically managing access of the users to the elevator services based on groups or floors. The management system may comprise software running on the remote server 302 and configured to provide instructions to the SACD 100.

In an embodiment, users may be compiled based on two or more groups depending on the compilation criteria which may comprise medical status, professional status, national origin, legal status and the like. Users belonging to a given group can be managed collectively by managing group elevator control rights, guiding and/or notifying them on floor selection for a particular elevator. The map may divide and illustrate the various categories of users, for example a red category and a green category, where users in the red category shall not mixed with users in the green category for various reasons (such as health or security reasons for example). Users in red (User Group A) can be managed collectively by mapping them to certain floors only and users in green category (User Group B) may be managed collectively by mapping them to certain other floors different from the floors for the group A. The floor selections for A and B may also be a different time period allocation to the different user groups A and B in relation to a same physical building. In an exemplary embodiment the access control unit 100 may divide the users into a technical and non-technical workers. The technical workers may be mapped to the second floor while the non-technical workers may be mapped to the first floor by the access control unit based on such pre-stored information and the user identifiers.

The processing of the user related data in view of the pre-stored information in order to map the identifier to a specific floor may be conducted locally at the level of the SACD 100 of an elevator, and it may also be conducted using a remote server 305 in communication with the SACD 100. The remote data processing unit/remote system/remote server 305 may be located on a data cloud network, and the communication with the SACD 100 can be conducted using any suitable communication technology such as TCP/IP, GSM, RF or LPWAN. The remote server 305 may be accessible to various SACDs 100 associated with several selected elevators installed in a premise. In an embodiment, the data cloud network may be accessible to the SACDs 100 associated with all or some selected elevators of a building, several buildings in a compound, or blocks, etc. It minimizes the need to maintain separate database for each of the SACDs 100 that otherwise may have common users. Such a system may lead to a central system 200 wherein the access control units 100 may be in wireless communication with each other and to a remote server 105 for sharing data.

In an embodiment, the access control unit 100 may comprise a GSM module for providing a data link to a remote network.

Figure 7:
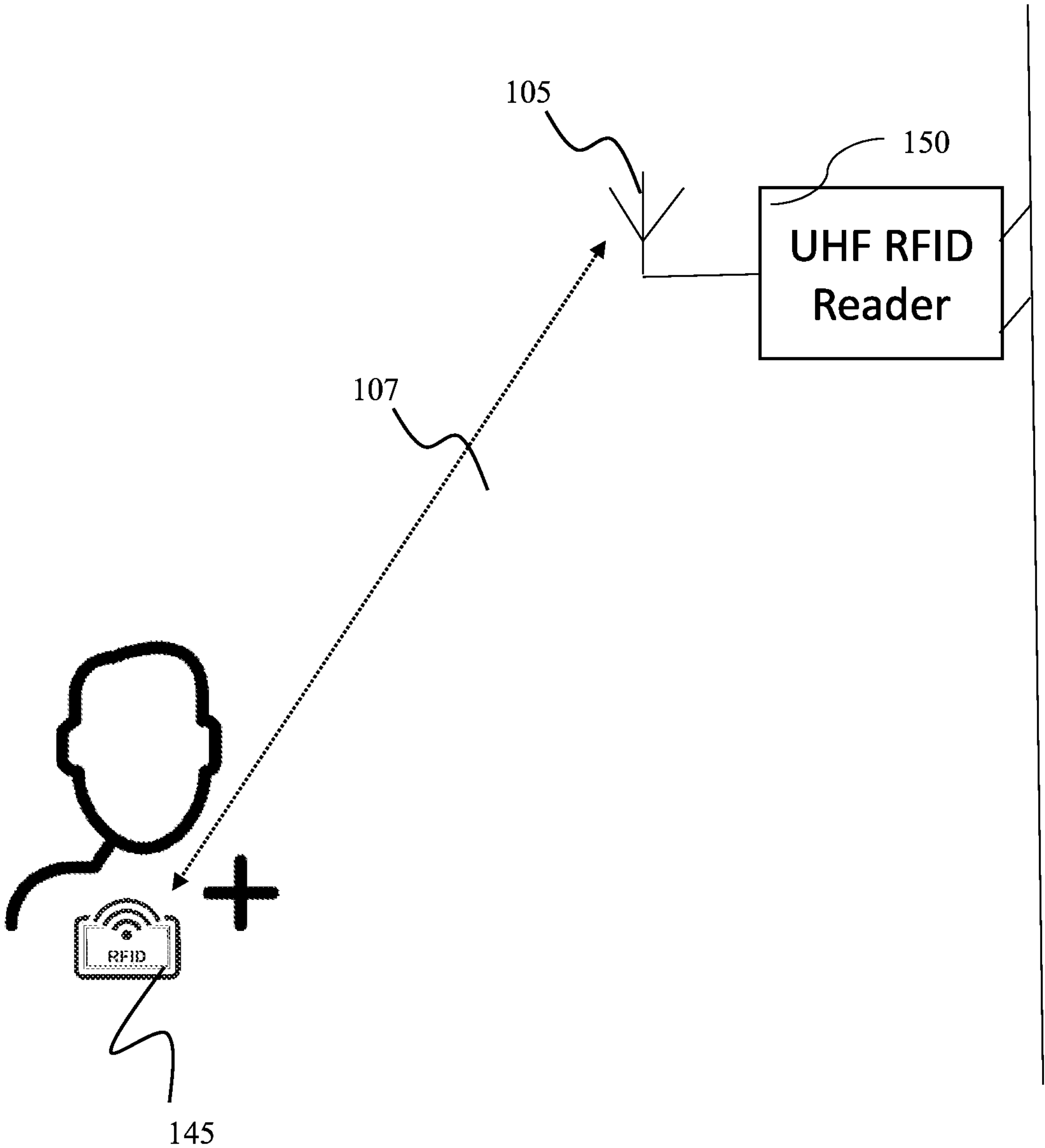
FIG. 7 is a schematic illustrating an RFID reader in communication with an RFID transceiver for elevators in accordance with an embodiment of the invention.

In an embodiment of the invention, and as illustrated in FIG. 7, the user device 50 may comprise a RFID transceiver 145 and the receiver 102 may comprise a RFID reader 150 configured to be in communication with the RFID transceiver 145. The RFID reader 150 may be configured to establish a data communication with the RFID transceiver 145 when the latter is within a proximity distance range 107 from the RFID reader 150. This is in order to ensure that the elevator floor selection and trip initiation is triggered only when the user is inside the elevator within a distance range 107 (and not while being outside the elevator). The RFID reader power and/or the associated antenna(s) 105 configurations may be adjusted to achieve this distance range 107. The RFID reader 105 may be placed at the ceiling of the elevator or one of the walls of the elevator cabinets, preferably above the door with the antenna(s) pointing towards the elevator cabinet wall opposite the door. The RFID reader maybe Ultra High Frequency (UHF) RFID reader, with an adjusted power and antenna design to capture only users within a specific elevator zone and distance range 107. The RFID transceiver 145 may comprise a passive RFID tag with a unique identifier which is mapped to the destination floor of the user and stored in the storage unit 70. In this case, the user, through the RFID-based user device 50, may be automatically and seamlessly be identified by the SACD 100 and automatically and seamlessly routed to the user's destination floor without any action or intervention by the user or any other human. The user will not be required to push an elevator button, pass an access card, connect to the elevator system through a mobile device, or conduct any action.

In an embodiment of the invention, the floor selection and the elevator car trip activation to the user's destination floor may be conducted automatically/seamlessly between the SACD 100, the elevator system 200 and the user device 50 without any user intervention or any other human intervention while the user/identification device 50 is inside the elevator or within the elevator proximity zone. Therefore, the present invention is aimed at eliminating such time gap and providing a seamless access control system for elevators wherein there is a direct connection between the elevator buttons or the elevator control panel in order to activate a floor for the user once the user identifier is received.

In an embodiment of the invention, each RFID identifier associated to a given user device 50 is linked to a given user and to maximum two destination floors, a first destination floor and a second destination floor. If only a single destination floor is associated to the identifier, then the user will always be routed to that specific single destination floor. However, in most cases, each user may have access to two floors in a building, a first floor which is normally a restricted floor accessible to the user (where his company is located for example), and a second floor which is normally a publicly accessible floor such as the Lobby for example. The question is how to determine the right destination floor among the first and second destination floors at any given time. The SACD 100 may be configured to detect the current floor number/level where the lift is positioned at the time an identifier associated to the user is detected. As the user has access to two floors only, the first and second destination floors, then the SACD 100 may route the user to the destination floor which is different from the current floor number/level where the lift is positioned. For example, if a user is linked to Floor G and Floor 5, the SACD 100 may route the user to Floor G whenever the lift is at the Floor 5 level, and my route the user to Floor 5 whenever the lift is detected to be at Floor G. The SACD 100 be connected to the elevator system 200 for receiving the current floor number/level of the lift.

In an embodiment, there is provided a remote controller 90 configured with dual features (also called dual personality user device), a first feature for a seamless detection and routing to a destination floor in accordance with the various embodiment of the present invention, and a second feature for manually triggering an elevator services request by the user using the user device in accordance with the various embodiments of the present invention. The remote controller 90 may be configured to establish two different communication channels with the SACD 100, a first communication channel which is established automatically between the user device 50 and the SACD 100 when the user device is detected within a specific elevator zone (preferably inside the elevator), and a second communication channel which is triggered manually by the user for requesting elevator services (this is for example through pushing a button on the user device, or entering his biometric data). The first communication channel is preferably RFID based communication, and more preferably an UHF RFID which detects the user device in a range of 2-3 meters. An RFID transceiver may be integrated within the user device for this purpose. The second communication channel is preferably a Radio Frequency (RF) based communication, preferably through a frequency between 300-450 MHz. The dual personality user device may be held the user for a seamless detection and routing to a destination floor when this service is possible (for example, when the system can determine with high level of likelihood the destination floor without any input by the user), and in case this service is not available, then it can be used for manually triggering by the user the elevator services through the user device. This dual personality user device can also be used for both unregistered and registered users. Both features may also be used simultaneously such that the seamless detection and routing feature may be triggered first through the first communication channel, and if more than one possible destination floor is available to the user and the system cannot decide the user's choice without the user's input, then the user may use the second communication channel to confirm his floor selection. The user interface may comprise a user interface, such as buttons, for this purpose according to the various embodiments of this invention.

In an embodiment of the invention, the SACD 100 may comprise an Artificial Intelligence based system comprising a machine-learning based algorithm which establishes floor trends for users based on their access details, comprising floors accessed during specific hours and so on. The SACD 100 or the user device 50 may comprise a user interface (not shown) for enabling the user to confirm or cancel a destination floor selection automatically made on his behalf by the SACD 100. The user interface (not shown) may comprise a touchless button or a gesture recognition device, based on a laser or infrared or ultrasound sensor for example, which may be used by the user to confirm or cancel a destination floor selection. As another example, the user interface (not shown) may also comprise a voice command module for receiving a voice command by the user. The user interface (not shown) may be used by the user to cancel a floor selection automatically made by the SACD 100 within a defined period of time, such as 3-5 seconds for example. If no cancellation is made within this predefined period of time, then a command signal will be passed by the SACD 100 to the elevator system 200 for automatically initiating an elevator car trip to the selected destination floor.

The SACD 100 may propose one or more floor selections to the user, and may require the user to confirm or reject a floor selection whenever more than one destination floor is determined by the SACD 100 to be a likely destination floor. The user may use the user interface (not shown) to confirm or reject one or more proposed floor selections made by the SACD 100. The user interface (not shown) may be connected to the processor 104 for conveying the user's input. The SACD 100 may only communicate with the elevator system 200 to confirm a destination floor selection once the user's input is made. Otherwise, the SACD 100 may cancel/reject the automated function of the floor selection and elevator trip initiation for the user which may be invited to use any conventional floor selection system available in the elevator.

In an embodiment of the invention, the user device 50 may be in communication with the RFID reader 150 through active wireless communication continuously transmitting user identifier signals and the user device 50 comprises a passive wireless communication transmitter, such as a RFID passive tag. According to this embodiment, the wireless technology used to communicate between the SACD 100 and the user device 50 is preferably Radio Frequency Identification (RFID). The determination by the SACD 100 on whether the user device 50 is within the elevator zone may be conducted based on the signal strength transmitted by the user device 50 and received by the SACD 100.

In an embodiment of the invention, the RFID reader 150 is preferably located at a suitable height from the ground such that the user device 50 is within a suitable wireless connectivity distance range when a user carrying or wearing/using the user device 50 passes through the specific elevator zone. Depending on the application, the SACD 100 can be provided with a support structure for receiving and positioning the RFID reader at the suitable height such that the user device 50 is positioned within the wireless connectivity distance range when the user is passing through the specific elevator zone. The RFID reader 150 may be configured/adapted to transmit signals having suitable wireless signal characteristics, including frequency and power, capable of being detected by the user devices 50 while these are within the specific elevator zone. The wireless technology and signal characteristics can vary depending on the application.

Figure 8:
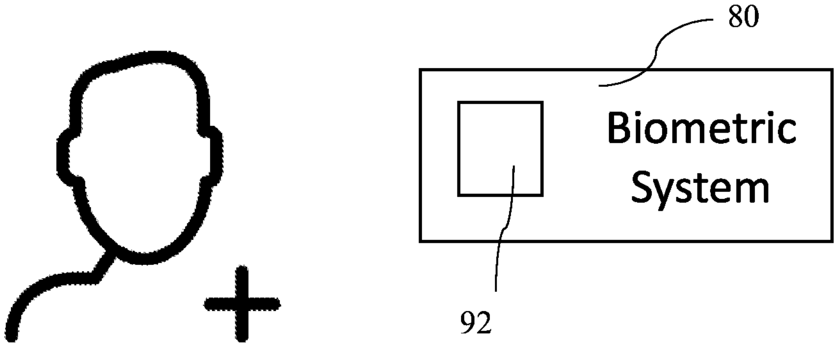
FIG. 8 is a block diagram illustrating a biometric system for elevators in accordance with an embodiment of the invention.

In an embodiment of the invention, and as illustrated in FIG. 8, the user device 50 may comprise a user recognition system positioned in proximity or inside the elevator which may be used to identify the users entering an elevator. The user recognition system, may comprise a biometric system for example such as a face recognition system. Users may be identified by the user recognition system using user related biometric data for example, and the user device 50 may automatically generate identifiers unique to the users which are sent automatically to the receiver 102 of the SACD 100. A single user device 50 may be used centrally by a plurality of users (instead of being allocated to each one of the users individually). The biometric recognition system 80 may be mounted in the elevator in proximity of the SACD 100. The data communication between the biometric recognition system 80 and the receiver 102 is either wired or wireless communication in this case.

The user device 50 according to the various embodiments of this invention may be a handheld device. The user device 50 may take various shapes, such as a universal remote controller shape for example. It can also take the shape of a pen, a pin or any other suitable shape. The user device 50 may be a handheld device comprising a finger print authentication unit (not shown). The user device 50 may only send an identifier to the SACD 100 after successful authentication of the user using the finger print. The user device 50 may in this case be in the shape of a remote controller with a screen to receive a user's finger for obtaining a finger print and comparing it to a pre-stored finger print of the user.

Figure 9A:
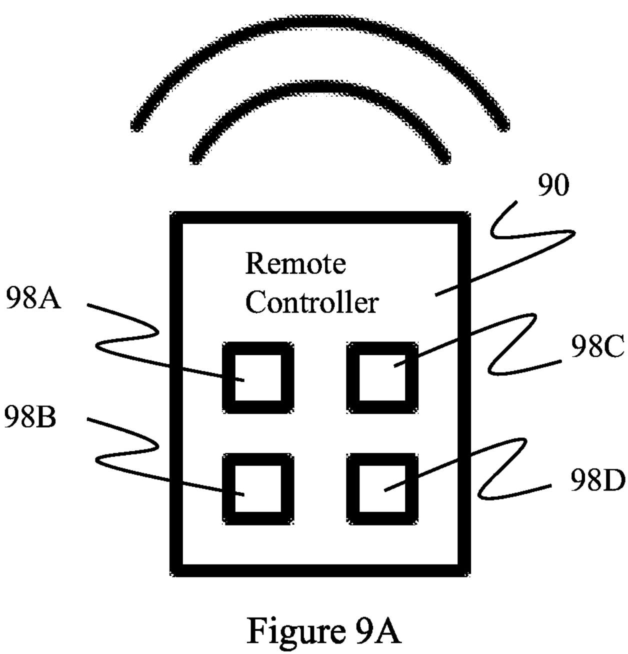
FIGS. 9A-9B illustrate a remote control device for elevators in accordance with an embodiment of the invention.
Figure 9B:
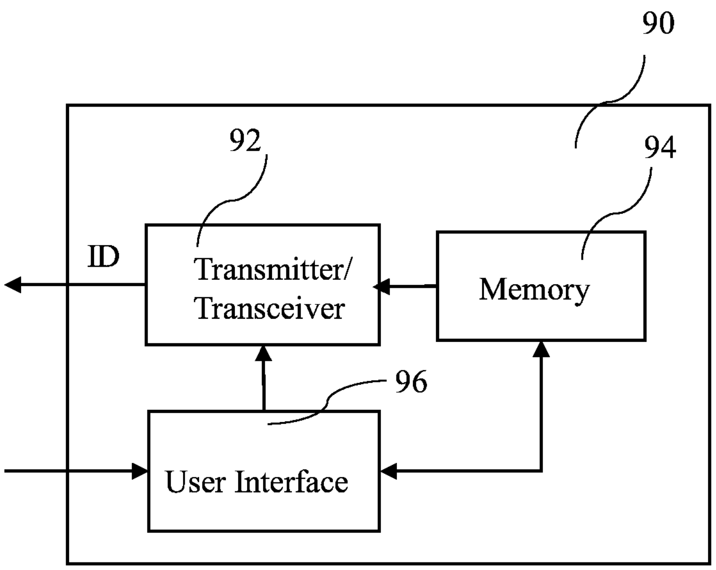

In an embodiment of the invention, and as illustrated in FIGS. 9A-9B, the user device 50 may consist of or comprise a wireless remote controller 90 adapted to be in wireless communication with the SACD 100 for enabling a user to wirelessly request an elevator car trip to one or more floors in a building. The remote controller 90 may comprise a user interface 96 configured to enable the user to select a destination floor, a memory 94 for storing unique identifiers corresponding to the various floors, and a transmitter 92 for transmitting the identifiers associated to the selected floors to the SACD 100. The transmitter may by a Radio Frequency (RF), Infrared (IR), RFID or any other suitable technology. The remote controller may be a universal remote controller. The transmitter 92 may be a RF transmitter, and it may have a frequency in the range of 300-450 MHZ.

The user interface 96 which may comprise one or more buttons (98A, 98B, 98C, 98D), for enabling the user to trigger elevator car trips to one or more floors. The one or more buttons may be configured with respective unique identifiers, such that each button may have a unique identifier different from another button identifier. Each button may be configured to enable the user access to a given floor. The one or more identifiers associated to the one or more buttons of the wireless remote controller may be mapped to corresponding destination floors such that each button is mapped to one specific destination floor. Data mapping the one or more identifiers associated to the buttons of the remote controller to the corresponding destination floors is stored in the storage unit 70. When the user pushes a button, the unique identifier corresponding to the pushed button is wirelessly transmitted to the SACD 100 which is received by the receiver 102 and sent to the processor 104 which queries the storage unit 70 using the identifier for retrieving the associated destination floor which is transmitted to the elevator system 200 for automatically initiating an elevator car trip to said destination floor.

The user device 50, such that the remote controller 90, may be used for buildings with restricted floor access. As an example, in a building shared by several companies, the company that occupies the second floor may wish to prevent employees and visitor of other companies within the building from accessing their floor. For hotels to provide a secure environment for their guests, it may be necessary to restrict access to the bedroom floors to paying guests and staff only, reducing the risk of theft and assault.

The user device 50, such as the wireless remote controller 90, may be used for buildings with restricted floor access. Users in a building may be provided with user devices 50, such as the wireless remote controllers 90, configured to enable them to initiate elevator car trips to their respective restricted floors, but not to other floors. Each user in a building with restricted floors may have access rights to a limited number of restricted floors only, such as one or two restricted floors. This is in addition to one or two general floors such as a ground floor and a parking floor.

Each user device 50 (such as remote controller 90) may be associated to one given user, and each user device 50 may be configured with one or more identifiers. Each one of the one or more identifiers associated to the user device 50 may be mapped to one given floor, among the restricted floors or the general floors, which is available to that given user. Each identifier may allow the given user to access one floor only, and not other floors. The one or more identifiers may be transmitted by the user device 50, such as the wireless remote controller 90, to the SACD 100 at the time of requesting elevator car trips by the user. The one or more identifiers associated to a given user device 50 (such as remote controller 90) may be mapped to one given user such as an identification of the one or more identifiers allows of identifying the corresponding given user. When the user activates a button of the user device 50 (such as the remote controller 90), for initiating an elevator trip to a given floor, the identifier associated to that button is transmitted to the SACD 100 which is used to query the storage unit 70 for retrieving the corresponding destination floor. The access details, such as the user ID, login date and time and elevator car ID may be stored in a database, which may be the storage unit, for future use by the facility management.

The user interface 50, such as the wireless remote controller 90, may be provided with a user interface 96 for enabling the user to initiate elevator car trips to the restricted floors to which he/she has access, and not to others. For example, if user A has access rights to Floor 5 in addition to the Ground Floor G, then a wireless remote controller (for example remote controller A) may be configured to enable user A to initiate elevator car trips to Floor 5 and Floor G only, and not to others. The wireless remote controller A may be provided with a user interface 58 for enabling the user to select the floor to which he/she wants to initiate an elevator car trip among the available floors only (Floor 5 and Floor G). For example, the user interface 58 may comprise two buttons, each button configured to initiate an elevator car trip to one of the two floors accessible to the user. A first button may be configured with a first identifier (identifier A) mapped to restricted Floor 5, and a second button may be configured with a second identifier (identifier B) mapped to general Floor G. The identifiers A and B are stored in the storage unit 70 in association with destination floors 5 and G respectively. Identifiers A and B may also be mapped to the remote controller A and to the user A such as an identification of the identifier A or identifier B allows to identifier the user A.

For example, a building having 10 floors and 1000 users may be provided with 1000 user devices 50, such as remote controllers 90, each one being mapped to one given user and one or more given floors. The user devices 50, such as the remote controllers 90, may comprise corresponding unique identifiers which are transmitted to the SACD 100 at the time users request elevator car trips to their desired floors. Each unique identifier may be associated to one specific user and one specific destination floor to which this specific user has access. Data mapping each unique identifier to a given user and a given floor may be stored in the storage unit 70. According to one example, each user device 50, such as the remote controller 90, may be used to access one floor only. In this case, each user device 50 (such as remote controller 90) would be configured with a single unique identifier. In this case, the storage unit 70 may store 1000 unique identifiers (1 identifier/remote controller) mapped to 1000 corresponding users and their respective floors to which they may have access.

According to another example, each user device 50, such as remote controller 90, may be used to access N floors. In this case, each remote controller may be configured with N unique identifiers such that each identifier is mapped to one floor among the N floors accessible to the users. In this case, the storage unit 70 may store N×1000 identifiers (N identifiers/remote controller) mapped to 1000 corresponding users and their respective N floors to which they may have access. For example, each remote controller 90 may be configured with 2 restricted floors and 2 general floors. In this case, four unique identifiers are required for each remote controller such that each identifier allows to identify one specific floor among the four floors available to the user. The four identifiers are all linked to the same user. An identification of any one of the four identifiers will allow to identify the user having initiated the elevator trip request which may be used for the access recording purposes inside an access database.

In an embodiment of the invention, the user interface 58 of the user device 50, such as the remote controller 90, may comprise other elevator functions such as elevator call up button and elevator call down button. Each one of these functions may be associated to an identifier which may be sent to the SACD for triggering a corresponding elevator function based on the identifier received. For example, an SACD 100 may be configured for the elevator call functions and which may be installed and connected to the elevator call panel, such that a receipt of an identifier corresponding to the elevator call up feature would activate the call up button of the elevator and a receipt of an identifier corresponding to the elevator call down feature would activate the call down button of the elevator.

In an embodiment of the invention, the user interface 96 of the user device 50, such as the remote controller 90, may be configured to enable a user to specify the exact floor number among N available floors inside the building. The user device 50, such as the remote controller 90, may store N unique identifiers corresponding respectively to the N floors. Based on the floor number selected by the user, the remote controller may retrieve the unique identifier associated to the selected floor number and send it to the SACD 100. The N unique identifiers may be stored in the storage unit 70 in association with their corresponding floors. At the time of receiving an identifier, the SACD 100 would query the storage unit 70 with the identifier received for retrieving the associated floor number which is used to automatically initiate an elevator trip to that specific floor.

In an embodiment of the invention, the user device 50, such as the remote controller 90, may be configured to enable the user to make a floor selection to any desired building floor (for example floors 1 to 35). The user interface 96 may for example comprise a keyboard to enable the user to input a floor number, or may comprise a screen with two arrows, a first arrow and a second arrow for respectively enabling the user to increment and decrement the numbers on the screen for floor selection. The user interface 96 may also comprise a confirmation/transmission button for enabling the user to confirm the floor number once it is entered by the user. The confirmation/transmission button may trigger the transmission of the identifier associated to the floor specified by the user to the SACD 100 which may query the storage unit 70 with the received identifier for retrieving the corresponding floor number. The SACD 100 may then communicate with the elevator system for automatically initiating a trip to the user to the destination floor as specified.

For buildings with unrestricted floors, there is no need to link the identifiers corresponding to the building floors with access rights associated to the users. In this case, all the user devices 50, such as the remote controllers 90, provided to the building users may be configured with the same unique identifiers such as each floor number has a corresponding same unique identifier across all the user devices 50, such as the remote controllers 90. The building/elevator floors may also be identified by the user device 50 through a modulation of signal frequency, signal amplitude/power, number of signals sent/captured by the receiver 102 or any other suitable technique. For buildings with restricted floor access, each request received from a user device 50, such as a remote controller 90, should be mapped to a specific user in order to determine a destination floor based on the access rights of the user. A way to achieve this is to link each user device 50, such as each remote controller 90, to a corresponding user specific accessible floor(s) such that each user device 50, such as each remote controller 90, is configured to initiate elevator car trips to destination floors accessible to its corresponding user only, and not to other floors. Alternatively, the user devices 50, such as the remote controllers 90, may be configured to enable users to select any floor number in a building, however the SACD 100 would only trigger the elevator system to initiate a trip when the floor selected by a user correspond to a floor accessible to the user as per the records stored in the storage unit 70. A floor access request originating from the user device 50, such as the remote controller 90, will need to be able to identify the user having originated the request. This may be through the floor identifier itself which may also be unique to the given user, or may be through a separate user identification.

In an embodiment of the invention, the user device 50 comprises buttons configured with pre-authorized elevator functions and/or destination floors. The user device 50 may comprise elevator call buttons, preferably an up button and a down button. The user device 50 may comprise one or more buttons where each button is configured to activate a destination floor accessible to the user. For example, a given user may have the right to access two given floors only inside a building (such as the Ground Floor and Floor 4) where all the other floors of the building are restricted access. In this case, a first button in the user device (button A) may be configured to trigger the activation of the Ground Floor and a second button in the user device (button B) may be configured to trigger the activation of Floor 4. The SACD automatically initiates elevator trips to these floors once the corresponding buttons in the user device are triggered by the user.

In an embodiment of the invention, each button is associated to a unique button identifier. Each button identifier is pre-stored in the storage unit in association with a given user and a given destination floor to which the user has access rights. The SACD automatically determines the destination floor based on the button identifier received from the user device. The destination floor is determined and stored inside the storage unit based on the user profile and access rights. The destination floor associated to a given button identifier may be modified from time to time based on the user's access rights. For example, when an employee is relocated from one floor to a second floor different form the first floor, management may reconfigure the destination floor associated to the user device button to link it to the second floor rather than to the first floor. The user does not have to specify the floor as this is pre-configured and pre-stored in advance in the storage unit.

The user device 50 may be a smart mobile device, such as an iPhone, or may be an electronic circuitry coupled to or integrated in a mobile device, or may be a mobile application running on a mobile device, or otherwise connected to a smart mobile device. The user device may comprise a coupling mechanism, such as an adhesive or a magnet, to couple/stick the user device on a mobile device of the user. The user device 50 may be removably coupled or attached or permanently integrated to a wearable, portable or movable device associated with the user. The wearable, portable or movable device associated with the user may comprise at least one of an accessory such as a bracelet, a ring, a watch, a pen, a key holder.

In an embodiment, the user device 50 may be associated with an official document such as a passport, an identity card, a smart card, a smart document or a protective equipment such as a protective clothing, a helmet, a face shield, a garment or an equipment designed to protect the user from communicating or contracting infectious diseases, such as COVID-19. According to an embodiment, the wearable, portable or movable device associated with the user comprises at least one of: a) an accessory such as a bracelet, a ring, a watch, a pen, a key holder; b) an official document such as a passport, an identity card, a smart card, a smart document; and c) a protective equipment such as a protective clothing, a helmet, a face shield, a garment or an equipment designed to protect the user from communicating or contracting infectious diseases, such as COVID-19. According to an embodiment, the identification device is adapted to be used in connection with one or more of a personal protective equipment such as a protective clothing, a helmet, a face shield, a garment or an equipment designed to protect the user from communicating or contracting infectious diseases.

In an embodiment, the user device 50 may be adapted to be used in connection with one or more of a personal protective equipment such as a protective clothing, a helmet, a face shield, a garment or an equipment designed to protect the user from communicating or contracting infectious diseases. In an embodiment of the invention, the SACD 100 may control (allow or restrict for example) access of the user to the elevator service as a function of a status of the user which may be determined as a condition precedent to initiating an elevator trip of the user to a destination floor. The determination of the status of the user may require using units which may comprise detectors, sensors, tracking devices, positioning devices, health & safety monitoring devices 106, mental/behavioral assessment devices, and other electronic components configured to obtain at least a part of the user related data. The user related data may also include existing databases such as immigration databases as mentioned above. It may also include medical databases to obtain medical data in relation to the users such as medical results for example, security or judicial clearance databases to obtain security data in relation to the users such as criminal records for example, governmental databases to obtain regulatory, legal or medical status of the users and so on. In an embodiment, a mobile device of the user may also be connected to track any information on the mobile device which may constitute an impact on safety and security and which may impact floor selection for the elevator.

Figure 10:
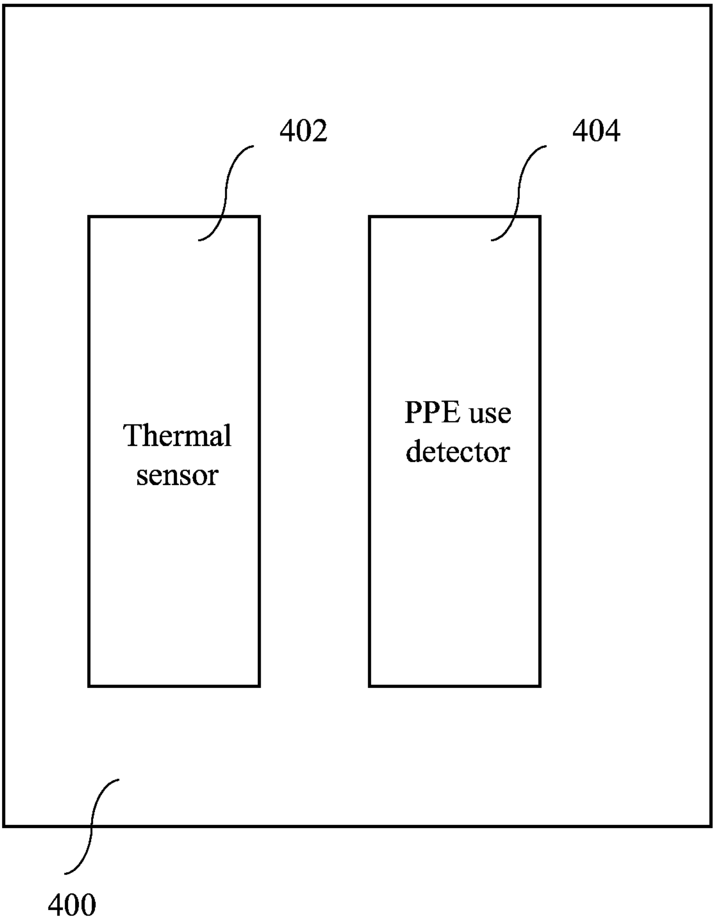
FIG. 10 illustrates a Health & Safety (H&S) Monitoring Unit in communication, or part of, the SACD for elevators in accordance with an embodiment of the invention.

In an embodiment, referring to FIG. 10, the SACD 100 may also consider additional user related data in order to grant access to the user. Said user related data may be real time data associated with the user or pre-stored data. For this purpose, the user device 50 and/or the SACD 100 may comprise or may be connected to may obtain data relative to collection devices which may comprise an a health & safety monitoring unit 400 monitoring the real time health & safety requirements of the user. In an embodiment, health condition of the user such as temperature, virus or bacterial infection, and any other biological, chemical, physiological or psychological condition may be monitored. The health and safety monitoring unit 400 may also comprise devices configured to monitor behavioral, psychological and/or physiological aspects related to the user such as nonverbal gestures which may be indicative of incompliance with a given pre-stored information such as a possible intention for a safety/security breach for example. The control of the automatic floor selection may also comprise enabling or disabling the users to make certain actions a priori, or enabling or disabling certain actions a posteriori conducted by the users. In an embodiment, the user related data may comprise a PPE use detector 402 to detect a proper use of a personal protective equipment by the user, and the H&S requirements comprise the user is properly using the personal protective equipment.

FIG. 10 illustrates a Health & Safety Monitoring unit 400 in accordance with an embodiment of the invention. In an embodiment, the PPE use detector 402 may determine whether the user is wearing/using the PPE or, in case the PPE is a smart user device having an adjustable face shield, whether the face shield is being secured. In another embodiment, the H&S Monitoring Unit 400 further comprises a thermal detector 404 for detecting a body temperature of the user, and the H&S requirements further comprise the user's body temperature is below a predefined temperature threshold.

The results as detected by the Health & Safety Monitoring unit 400 may be stored in the storage unit 70 for consideration by the SACD 100. In case there is compliance of the user with the health & safety requirements, the processor 104 may transmit the command signals with floor selection to the elevator system 200. In the other case, the SACD 100 may reject access to the user to the elevator services.

In an embodiment of the invention, the user device 50 may comprise a bracelet (or a ring or another accessory) comprising a heat sensor configured to be wore by the user and further configured to take the temperature of the user from the user's body, such as the user's arm/wrist or finger while being wore. The user device 50 may be configured to send an access request to the SACD 100 only when/if the user's temperature is below a predefined threshold (such as 38 degrees Celsius). The access request may comprise an identifier for use to determine a destination floor and grant user access to the elevator services.

The SACD 100 may also be connected to a notification device to notify the users or third parties about the floor selection associated to the user. The SACD 100 may comprise the notification unit for communicating with the users. For example, a digital display unit may be positioned outside the elevator connected to the processor 104 for displaying the status of the floor selection and whether the user is authorized to operate or take the elevator trip. For example, passengers or drivers who have not taken a virus vaccine may not be authorized to take an elevator trip. The user device 50 such as a mobile phone device may also issue a notification in case the user is not allowed to access a particular elevator.

Figure 11:
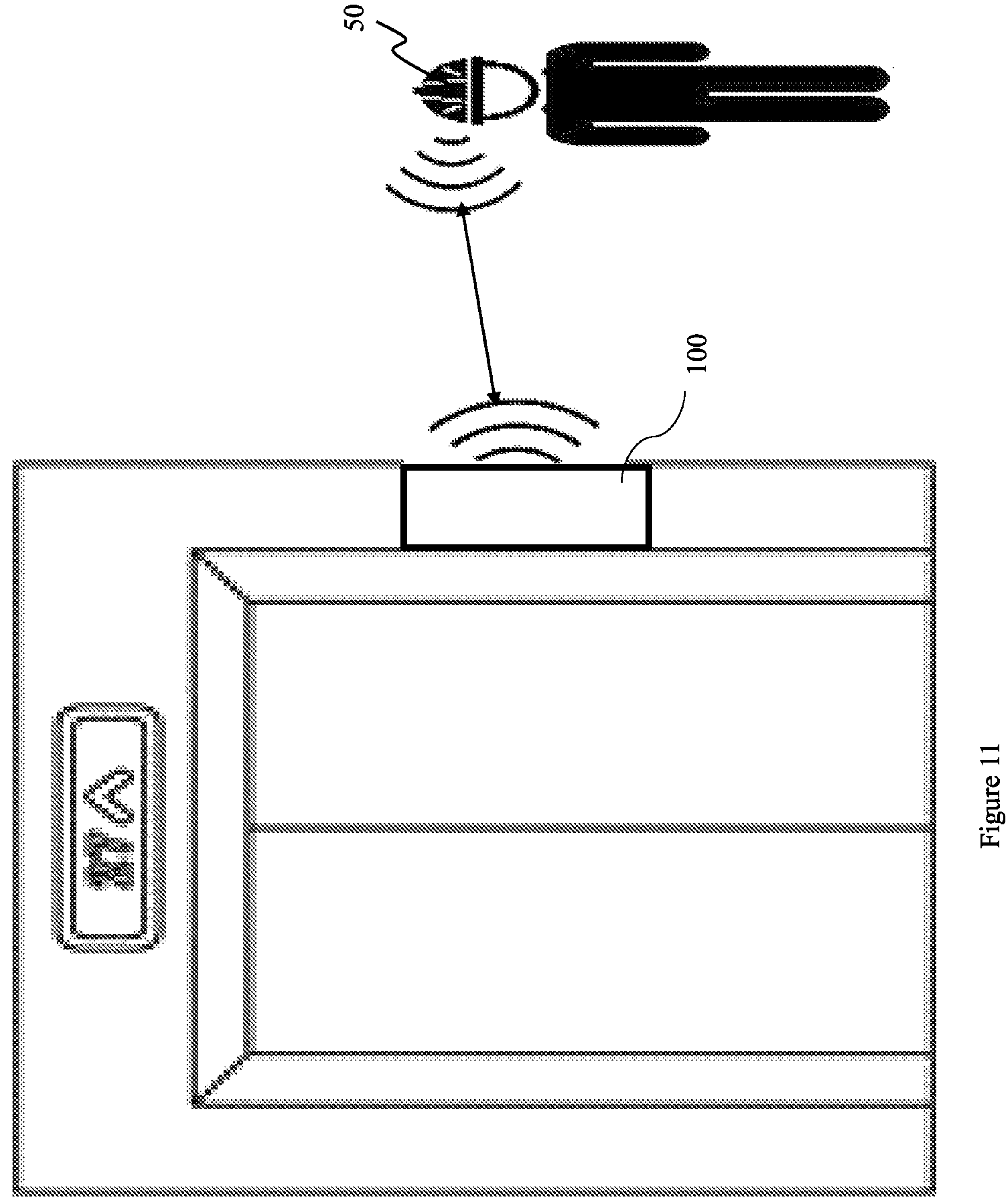
FIG. 11 illustrates a smart lift (elevator) equipped with a SACD designed to be in communication with a user device, which is a smart face protective devices (SFPDs) for illustration purposes, for controlling access to the building (controlled zone) according to an embodiment of the invention.

As illustrated in FIG. 11, in an embodiment of the invention, there is provided a smart elevator comprising a SACD in communication with user devices 50 for access control to elevators in accordance with the various embodiments of the present invention. According to the illustrated example, the user device 50 may comprise a safety helmet or smart face protective device (SFPD). In an embodiment of the invention, the SACD 20 is connected to the keyboard (or keyboard panel circuit) of the elevator for receiving a user desired floor and automatically sending a floor request to the lift keyboard (or keyboard panel circuit) without any touch by the user. The floor number can be stored inside the SFPD memory 38 and automatically communicated to the SACD 20 during the authentication/access control process. The floor associated to the user can also be specified by the user at the time of accessing the elevator through a user interface.

Figure 12:
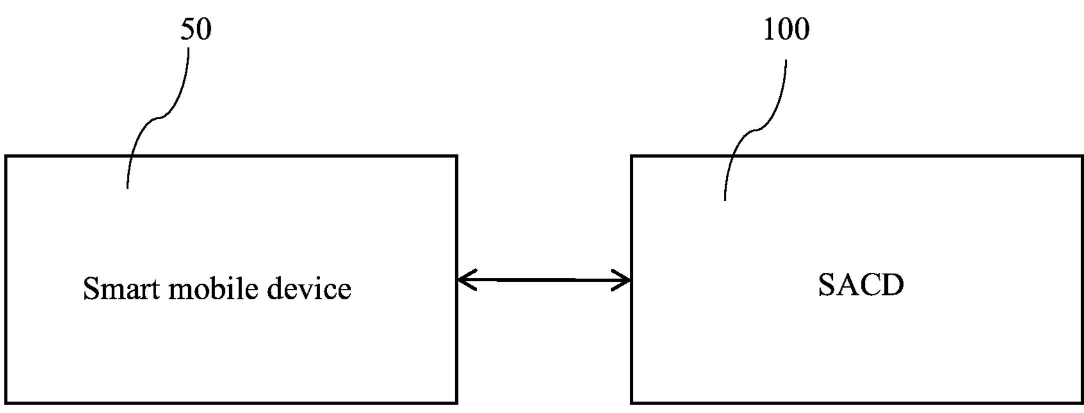
FIG. 12 illustrates use of smart mobile device as user device for communication with the SACD for elevators in accordance with an embodiment of the invention.
Figure 13:
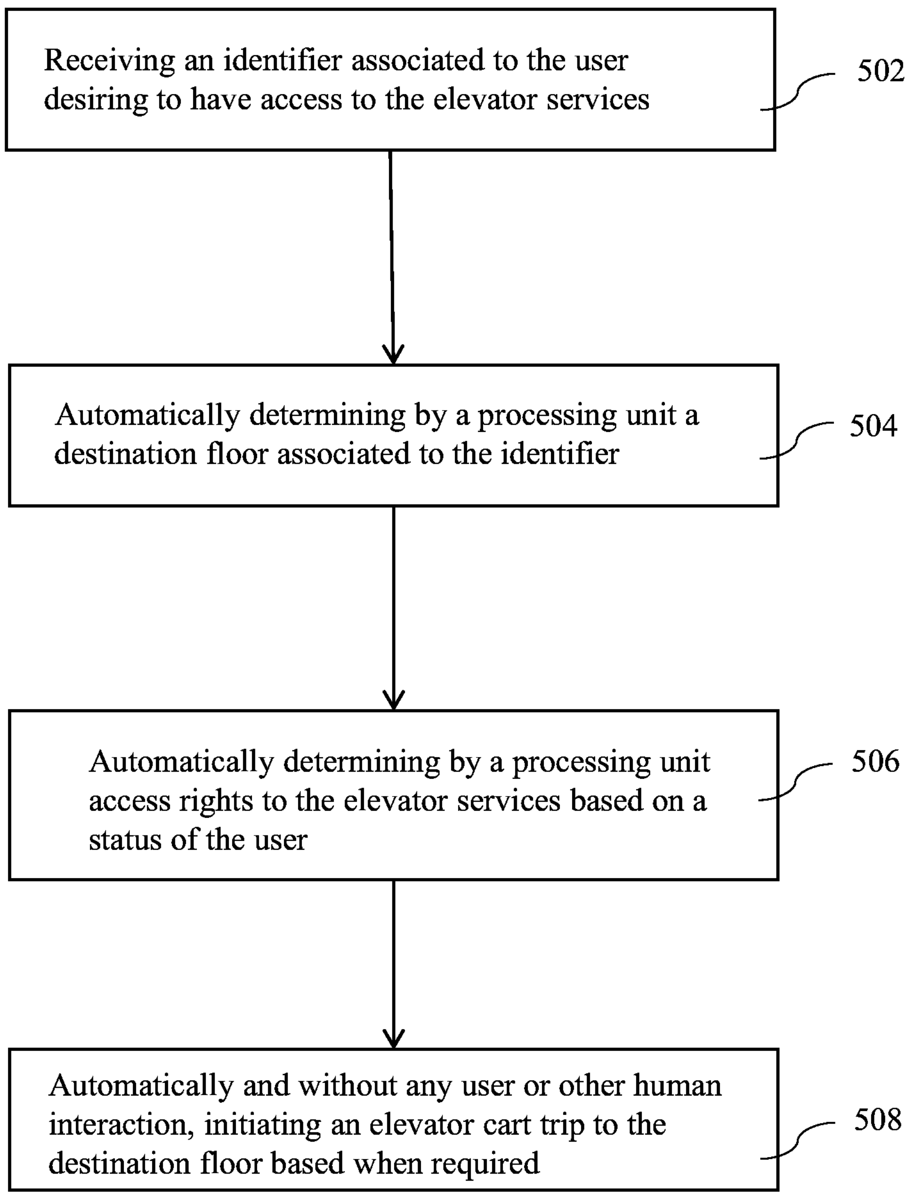
FIG. 13 is a flow chart illustrating an automated process for elevator access control in accordance with an embodiment of the invention.

As illustrated in FIG. 12, the user device may comprise or consist of a smart mobile device, such as a mobile phone, in accordance with the various embodiments. The mobile device may act as a remote controller using integrated technology, such as infrared IR remote control, or using a proxy device. The user enters the specific elevator zone and triggers the receiver manually by pressing button on the mobile phone device at the specific mobile application installed in the mobile phone device. As illustrated in FIG. 13, there is provided a computer-implemented process for access control to an elevator, comprising: Receiving an identifier associated to the user desiring to have access to the elevator services; Automatically determining by a processing unit a destination floor associated to the identifier; Automatically determining by a processing unit access rights to the elevator services based on a status of the user; Automatically and without any user or other human interaction, initiating an elevator cart trip to the destination floor based when required. The computer-implemented process may be conducted in accordance with the various embodiments of the present invention as explained with respect to the various features and functionalities with respect to systems and devices.

Many changes, modifications, variations and other uses and applications of the subject invention will become apparent to those skilled in the art after considering this specification and the accompanying drawings, which disclose the preferred embodiments thereof. All such changes, modifications, variations and other uses and applications, which do not depart from the spirit and scope of the invention, are deemed to be covered by the invention, which is to be limited only by the claims which follow.

The invention claimed is:

1. A smart access control device (SACD) for access control to an elevator system, the SACD comprising a receiver, a processing unit, and a communication unit for receiving by the receiver an identifier from a user device associated to a user and for automatically authenticating the user to be a pre-approved user and determining a destination floor associated to the user by the processing unit based on the identifier received and access control data stored in a storage unit accessible to the processing unit, and for generating and transmitting a signal to the elevator system for automatically initiating an elevator car trip for the user to the destination floor determined by the processing unit, wherein the user device is automatically detected, and the identifier is automatically transmitted from the user device to the SACD when the user device is within a specific elevator zone and is configured with a health & safety (H&S) monitoring unit to detect health or safety conditions of the user for compliance purposes, and the determination of the destination floor and the signal generation and transmission to the elevator system for automatically initiating an elevator car trip are automatically conducted seamlessly without any user or other human interaction, wherein determining the destination elevator floor accessible to the user is done automatically based on the identifier received from the user device.

2. The SACD of claim 1, wherein the access control data comprises identifiers related to user devices mapped to corresponding destination floors.

3. The SACD of claim 1, wherein the identifiers are unique identifiers such as each identifier allows to uniquely identify at least one of the user of the destination floor.

4. The SACD of claim 1, wherein the storage unit is a cloud-based storage unit, and wherein the SACD further comprises a communication unit in remote communication with the cloud-based storage unit.

5. The SACD of claim 1, wherein the receiver comprises an Ultra High Frequency RFID reader configured to detect the user device only when the user device is within the specific elevator zone.

6. The SACD of claim 5, wherein the specific elevator zone is within an elevator car.

7. The SACD of claim 6, wherein the automatically initiating an elevator car trip for the user to the destination floor is conducted seamlessly without any user or other human interaction.

8. A user device configured to be in communication with a smart access control device (SACD) for access control to an elevator system, the SACD automatically authenticating a user to be a pre-approved user and determining a destination floor and triggering an elevator car trip associated to the user to the destination floor based on an identifier received from the user device using said communication and access control data stored in a storage unit accessible to the SACD, wherein the user device comprises a health and safety monitoring unit configured to detect a health or safety condition associated to the user, wherein the SACD controls access of the user to the elevator system based on the detected health or safety condition of the user for compliance purposes, and the determination of the destination floor and the signal generation and transmission to the elevator system for automatically initiating an elevator car trip are automatically conducted seamlessly without any user or other human interaction, wherein determining the destination elevator floor accessible to the user is done automatically based on the identifier received from the user device.

9. The user device of claim 8, wherein the communication between the user device and the SACD is a wireless communication.

10. The user device of claim 8, wherein the identifier is a unique identifier allowing to uniquely identify at least one of the user and the destination floor.

11. The user device of claim 9, wherein the user device is a remote control comprising a user interface for triggering the communication with the SACD and a transmitter for transmitting the identifier through the communication.

12. The user device of claim 11 further comprising a biometric unit for authenticating the user prior to and as a condition to communicating with the SACD.

13. The user device of claim 9, wherein the user device comprises an RFID transceiver and the identifier is an RFID identifier, and wherein the user device is a wireless remote controller.

14. The user device of claim 8 comprising a biometric system for identifying the user based on biometric data obtained from the user.

15. The user device of claim 8, wherein the health & safety monitoring unit comprises a temperature sensor for detecting a temperature of the user, and wherein access to the elevator system is only granted if the user's temperature detected is below a given threshold.

16. The user device of claim 15, wherein the user device is a wearable device selected from the group consisting of a ring and a bracelet.

* * * * *